United States Patent

Fourtillan et al.

[11] Patent Number: 6,066,663
[45] Date of Patent: May 23, 2000

[54] OXIDATION DERIVATIVES OF INDOLYLALKYLAMINES AND THEIR USE AS DRUGS

[75] Inventors: Jean-Bernard Fourtillan; Marianne Fourtillan, both of Migne-Auxances; Jean-Claude Jacquesy, Buxerolles; Marie-Paule Jouannetaud, Poitiers; Bruno Violeau, Marcay; Omar Karam, Poitiers, all of France

[73] Assignees: CEMAF, Migne-Auxances; Laboratories Besins-Iscovesco S.A., Paris, both of France

[21] Appl. No.: 09/043,301

[22] PCT Filed: Sep. 17, 1996

[86] PCT No.: PCT/FR96/01444

§ 371 Date: Aug. 11, 1998

§ 102(e) Date: Aug. 11, 1998

[87] PCT Pub. No.: WO97/11056

PCT Pub. Date: Mar. 27, 1997

[30] Foreign Application Priority Data

Sep. 18, 1995 [FR] France .................................. 95 10900

[51] Int. Cl.[7] .................... A01N 43/38; C07D 209/44; C07D 209/46
[52] U.S. Cl. ............................ 514/418; 548/473; 548/472
[58] Field of Search .................... 548/473, 472; 514/418, 548

[56] References Cited

FOREIGN PATENT DOCUMENTS 0 527 687   2/1993   European Pat. Off. .
94/03427    2/1994   WIPO .

OTHER PUBLICATIONS

Fourtillan, J.B. et al., Preparation of Spiro (indole–3,3'–pyrrolidine) Derivatives as Melatoninergic Agonists, Chemical Abstracts, vol. 124, No. 13, Abstract No. 175864 (1996).

*Primary Examiner*—Johann Richter
*Assistant Examiner*—Dominic Keating
*Attorney, Agent, or Firm*—Finneagan, Henderson, Farabow, Garrett & Dunner, L.L.P.

[57] ABSTRACT

The invention relates to derivatives of general formula I

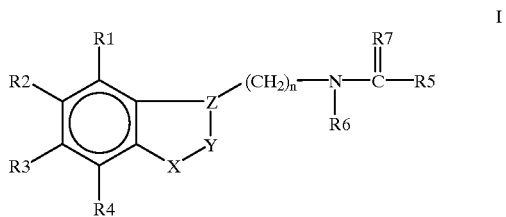

The invention also relates to pharmaceutical and cosmetic compositions comprising derivatives of general formula I.

19 Claims, No Drawings

OXIDATION DERIVATIVES OF INDOLYLALKYLAMINES AND THEIR USE AS DRUGS

The present invention relates to novel oxidation derivatives of indolylalkylamines, which are melatoninergic agonists, to a process for their preparation and to their use as drugs.

Melatonin, N-acetyl-5-methoxytryptamine, is a hormone from the pineal gland, isolated by Lerner et al. (J. Am. Chem. Soc., 80, 1958, 2587), and has been the subject of many studies for its circadian activity, in the rhythm of sleep, for its effects on the production of testosterone, for its activity on the hypothalamus and in psychiatric disorders.

It has thus been envisaged to use melatonin and its analogues in particular for the treatment of depression and psychiatric disorders, in particular stress, anxiety, depression, insomnia, schizophrenia, psychoses and epilepsy, and also for the treatment of sleeping disorders associated with travelling ("jet lag"), neurodegenerative diseases of the central nervous system such as Parkinson's disease or Alzheimer's disease, for the treatment of cancers, or alternatively as a contraceptive or as an analgesic.

However, the direct use of melatonin in vivo has not proven to be very satisfactory, given that a first passage through the liver extracts more than 90% of the active principle.

Various melatonin analogues have been described, demonstrating two routes of research focused either on the substituents of melatonin (WO-A-89/01472, U.S. Pat. No. 5,283,343, U.S. Pat. No. 5,093,352 or WO-A-93/11761), or on the aromatic ring by replacing the indolyl group by a naphthyl (FR-A-2 658 818, FR-A-2 689 124).

The present patent application thus relates to the preparation and use, as drugs, of novel oxidation derivatives of indolylalkylamines.

The present invention thus relates to novel derivatives of general formula I

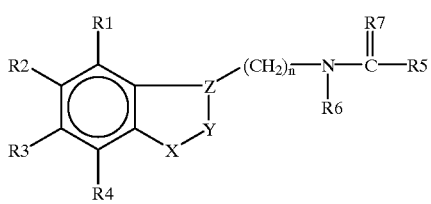

in which:

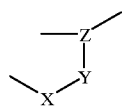

represents one of the following three radicals:

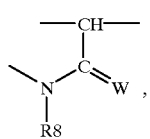

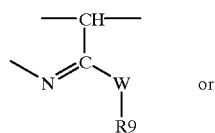

or

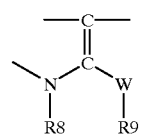

n is equal to 1, 2 or 3, preferably 2,

R1, R2, R3 and R4 represent, independently of each other, a hydrogen atom, a hydroxyl radical, a lower alkyl, cycloalkyl, lower alkoxy, aryloxy, lower aralkoxy, lower perhaloalkyl, lower perhaloalkoxy, halo or nitro radical or an unsaturated aliphatic chain, R5 represents a hydrogen atom, a lower alkyl, aryl or lower aralkyl radical, each optionally substituted with one or more halogens, an amino, (lower)alkyl-amino or (lower)dialkyl-amino, arylalkylamino, aralkylamino or diaralkylamino radical or a lower alkoxy, (lower)alkyloxycarbonyl, aryloxycarbonyl or aralkyloxycarbonyl radical, R6 and R8 represent, independently of each other, a hydrogen atom, a lower alkyl, aryl, lower aralkyl, lower alkoxy, aryloxy, lower aralkoxy, lower perhaloalkyl, (lower)perhaloalkyl-carbonyloxy, halo, alkylsulphonyl, arylsulphonyl, aralkylsulphonyl or (lower)perhaloalkylsulphonyl radical, W and R7 represent, independently of each other, an oxygen atom or a sulphur atom, R9 represents a lower alkyl, aryl or aralkyl radical, optionally substituted with one or more halogens, an alkylcarbonyl, arylcarbonyl, aralkylcarbonyl, (lower)perhaloalkyl-carbonyl or perhaloaralkyl-carbonyl radical, or a (lower)alkyl-sulphonyl, arylsulphonyl, aralkylsulphonyl, (lower)perhaloalkyl-sulphonyl or perhaloaralkylsulphonyl radical, it being possible for R5 and R6, R5 and R8, R6 and R8 and R8 and R9 to be linked to form a saturated or unsaturated ring containing at least 5 atoms and preferably 6, it being possible for this ring to contain several hetero atoms and to be substituted with one or more groups which may be, independently of each other, a hydroxyl radical, a lower alkyl, lower alkoxy, aryloxy, lower aralkoxy, halo or nitro radical or an unsaturated aliphatic chain, it being possible for R1 and R2, R2 and R3, and R3 and R4 to form part of another aromatic or non-aromatic ring with or without a hetero atom, containing at least 5 and preferably 6 atoms, it being possible for this ring to contain several hetero atoms and to be substituted with one or more groups which may be, independently of each other, a hydroxyl radical, a lower alkyl, lower alkoxy, aryloxy, lower aralkoxy, halo or nitro radical or an unsaturated aliphatic chain, their racemic mixtures, their pure enantiomers or their mixtures in all proportions, and their therapeutically acceptable salts.

The expressions lower alkyl, lower alkoxy and lower perhaloalkyl are generally understood to refer to radicals whose alkyl residue comprises between 1 and 6 carbon atoms.

These are preferably linear or branched C1–C4 alkyl residues chosen more particularly from the methyl, ethyl, n-propyl, isopropyl, n-butyl, isobutyl or t-butyl groups.

The term aryl is generally understood to denote aromatic and heteroaromatic groups, in particular aryls chosen from the phenyl, thienyl, furyl, pyridyl and naphthyl groups.

The aryl radicals may also be substituted with one or more substituents chosen in particular from the lower alkyl, lower alkoxy and halo radicals defined above.

The expression lower aralkyl will be understood to refer to the combination of a lower alkyl and an aryl as defined above. This will preferably be the benzyl radical, which may be substituted.

The halo radicals are preferably chosen from the fluorine, chlorine, bromine and iodine atoms.

The perhalo radicals are preferably perfluoro radicals.

Preferably, when R1–R2, R2–R3 and R3–R4 form part of another aromatic ring, with or without a hetero atom, this is another benzene ring, which may be substituted, or a pyridyl ring, which may be substituted.

When R1–R2, R2–R3 and R3–R4 form part of another non-aromatic ring, they together preferably form a divalent radical of formula —O—(CH$_2$)$_m$—, m being equal to 2 or 3, which may be substituted, or a divalent radical of formula —O—(CH$_2$)$_p$—O—, p being equal to 1 or 2, which may be substituted.

When the derivatives according to the invention comprise at least one asymmetric carbon of R or S configuration, the present invention also relates to the racemic mixtures of the derivatives of general formula I, as well as its pure enantiomers, or their mixtures in all proportions.

The therapeutically acceptable salts of the derivatives according to the invention are the usual organic or inorganic salts of the art, in particular the hydrochlorides, tosylates, mesylates and citrates as well as the solvates such as the hydrates or hemihydrates of the compounds of general formula I.

The present invention relates more particularly to the derivatives of general formula I for which W and R7 represent an oxygen atom and for which n is equal to 2.

Advantageously, at least one of the substituents R2 or R3 is other than a hydrogen atom and preferably represents a hydroxyl or lower alkoxy radical, in particular a methoxy radical.

Preferably, R1, R4 and R6 represent a hydrogen atom, and R8 or R9 represent, independently of each other, a hydrogen atom or a lower alkyl radical.

The present invention relates to the process for the preparation of the derivatives of general formula I as defined above, which are obtained by oxidizing, according to the usual methods, indolylalkylamines preferably with n=2, and:

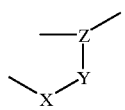

represents the radical Ia.

EXAMPLE 1

Formula: C$_{13}$H$_{16}$N$_2$O$_3$ M=248.28 g mol$^{-1}$
N-[2-(5-methoxy-2-oxo-2,3-dihydroindol-3-yl)ethyl]-acetamide To a solution of melatonin (1 mmol) in DMSO (1 eq.) is added 12N hydrochloric acid (2 eq.). The mixture is left stirring overnight at room temperature. 1 ml of water is then added, followed by aqueous ammonia solution (32%) until the mixture is neutral. The mixture is extracted with ethyl acetate. After evaporation of the solvent, the product is washed with ether.

Melting point: 160–3° C. NMR: $^1$H (CDCl$_3$, DMSO d-6, 1/1): 1.88 (s, 3H, NCOCH$_3$); 2.07 (m, 2H, CH$_2$ β to the acetamide); 3.23–3.45 (m, 3H, H-3 and —CH$_2$N); 3.74 (s, 3H, OCH$_3$); 6.72 (m, 2H, H-4 and H-6); 6.94 (s, 1H, H-7); 7.81 (broad s, 1H, NH of the amide); 10.1 (broad s, 1H, H-1). $^{13}$C (CDCl$_3$, DMSO d-6, 1/1): 177.6 (C-2, C=O oxindole); 168.4 (C=O, amide); 153.6 (C-5); 134.5 (C-7a); 129.2 (C-3a); 110.9, 109.9 and 108.2 (C-4, 6 and 7); 54.1 (OMe); 42.4 (C-3); 34.7 (—CH$_2$N); 28.8 (CH$_2$ β to the acetamide; 21.3 (methyl of the amide).

EXAMPLE 2

Formula: C$_{14}$H$_{18}$N$_2$O$_3$ M=262.30 g mol$^{-1}$
N-[2-(5-methoxy-1-methyl-2-oxo-2,3-dihydroindol-3-yl)ethyl]acetamide Melatonin (600 mg) is dissolved in DMSO (2 ml) in a 25 ml round-bottomed flask and potassium hydroxide (6 pellets≈300 mg) is then added. After stirring for 15 min, methyl iodide (0.6 ml) is added. The mixture is stirred overnight, diluted with water and then acidified with 2N hydrochloric acid. After extraction (dichloro-methane, 3 times), washing with acidified water, drying over magnesium sulphate and evaporation of the solvent, N-[2-(5-methoxy-1-methyl)indol-3-yl]ethylacetamide is obtained.

To a solution of N-[2-(5-methoxy-1-methyl)indol-3-yl)]ethylacetamide (1 mmol) in DMSO (1 eq.) is added 12N hydrochloric acid (2 eq.). The mixture is left stirring overnight at room temperature. 1 ml of water is then added, followed by aqueous ammonia solution (32%) until the mixture is neutral. The mixture is extracted with ethyl acetate. After evaporation of the solvent, the product is washed with ether.

NMR: $^1$H (Acetone d-6): 1.87 (s, 3H, NCOCH$_3$); 2.01 (m, 2H, CH$_2$ β to the acetamide); 3.11 (s, 3H, N—CH$_3$); 3.21–3.45 (m, 3H, H-3 and —CH$_2$N); 3.75 (s, 3H, OCH$_3$); 6.81 (m, 2H, H-4 and H-6); 7.05 (s, 1H, H-7); 7.56 (broad s, 1H, NH of the amide). $^{13}$C (CDCl$_3$): 177.1 (C-2, C=O oxindole); 170.2 (C=O, amide); 155 (C-5); 137.4 (C-7a); 129.6 (C-3a); 112.1, 111.1 and 108.0 (C-4, 6 and 7); 55.4 (OMe); 43.7 (C-3); 36.6 (—CH$_2$N); 29.1 (CH$_2$ β to the acetamide); 25.8 (methyl on indole nitrogen); 22.5 (methyl of the amide).

Biological activity

The hypnotic and sedative effects of the derivatives according to the invention, prepared above, were compared with those of three reference products, diazepam, pentobarbital sodium and melatonin, in chicks of the strain chair label JA657, which are 10 to 14 days old on the day of the test. The tests are carried out on chicks subjected either to programs of permanent lighting for at least 7 days from the day of the test, or to programmes of alternate lighting consisting of 12 h of darkness (20.00 h to 8.00 h) and 12 h of light (8.00 h to 20.00 h) for at least 7 days from the day of the test. For the two programmes, the lighting is provided by a halogen lamp (300 W) placed 30 cm above the floor of the vivarium. The tests are carried out between 14.00 h and 15.00 h. During the tests, the live weight of the chicks ranged between 85 and 120 g.

The chicks are allotted, in groups of 3, into identical 30 cm×50 cm×30 cm vivaria. The test products are administered intramuscularly (IM) into the pectoralis major muscle, as an aqueous-ethanolic solution (50/50 V/V ethanol/distilled water mixture), in a proportion of 0.2 ml of ethanolic solution per 100 g of live weight. The doses administered for the test products (novel compounds of the invention and reference substances) are equal to 1 or 2 μmol per 100 g of live weight. The placebo corresponds to 0.2 ml of the ethanol/distilled water mixture (aa) per 100 g of live weight. Since ethanol is used as solvent, its effect was compared beforehand with that of physiological saline (NaCl solution at a concentration of 0.9 p. 100) or distilled water.

The aqueous-ethanolic solutions of the test products were prepared at the time of use by successive dilution of a stock solution, obtained from 10 to 20 μmol of accurately weighed product, to which is added 1 ml of pure ethanol and which is agitated by ultrasound and then made up to 2 ml with 1 ml of distilled water for an injectable preparation. Tables I and II show the results obtained after IM administrations of doses equal to 1 and 2 μmol of the test products, dissolved in 0.2 ml of the ethanol/water mixture, per 100 g of live weight, to chicks subjected to programs of alternate or permanent lighting. For each chick, the volume injected is adjusted, according to the actual live weight, to 0.2 ml per 100 g of live weight. The parameters observed are the locomotor activity and the state of consciousness of the chicks over 2 h, which is equivalent to 6 theoretical wake-sleep cycles for a chick of this age. They are recorded by video camera for 90 minutes (tests under alternate lighting) to 260 minutes (tests under permanent lighting).

Five stages of alertness were defined:
stage 1: active wakefulness;
stage 2: animal lying down, head maintained with tonicity, eyes open;
stage 3: light sleep, animal drowsy: eyes closed with intermittent opening, immobile posture not modified by stimulation;
stage 4: deep sleep lying down: relaxation of the neck, characteristic posture of the head under the wing or hanging backwards;
stage 5: sleeping standing up: eyes closed, immobile, head dropped (catatonic).

These five stages correspond approximately to the stages of alertness and sleep defined in the examination of the electroencephalographic traces in this species. The correspondence is as follows:
deep sleep lying down: stage 4="slow wave sleep" (SWS)
sleeping standing up="sleep-like state I" (SLSI).

The drowsy stage 3 could correspond to paradoxical phases of sleep, with movement of the head, for example.

The chicks are observed by a trained observer with continuous video monitoring for at least 1 hour after the animals wake up.

Two stimuli were used to confirm the observations of the behaviour of the chicks at regular intervals:
the noise caused by tapping a plastic object on the glass of the vivarium, comparable to that of the beak of a chick on the glass, corresponds to a moderate stimulus. It is performed at each period of observation (i.e. every 5 minutes);
and the presentation of a metal feeder filled with the usual feed, left in the vivarium for 2 minutes. This is a powerful stimulus which calls upon sight, hearing and smell. It is performed every 15 minutes, that is to say at least 6 times in each test.

Waking up is defined by the appearance of the conscious elaborate behavior of searching for and consumption of food or drink.

The sleep time (ST) is defined by the sum of the durations of the phases of light sleep (stage 3), deep sleep (stage 4) and sleeping standing up (stage 5). The sedation time, following waking up, corresponds to stage 2.

The falling-asleep time (FAT) is equal (to the nearest minute) to the time required to pass from the state of active wakefulness (stage 1) to a non-alert state (stages 3, 4 and 5).

The hypnotic and sedative effects of the test products on the diurnal activity of 10- to 14-day-old chicks subjected, for at least 7 days, either to a program of permanent lighting (Table I) or to a program of alternate lighting (Table II) of 12 h of day (8.00 h–20.00 h) and 12 h of darkness (20.00 h–8.00 h) are given in Tables I and II. The tests are performed during the day between 14.00 h and 15.00 h.

For each test product, several series of measurements were made on batches of 3 animals, each value indicated in the Tables being the average in each batch of 3 chicks. When the number of batches is greater than or equal to 2, the figures indicated are the average limit values observed.

TABLE I

Tests under permanent lighting with administration of the products between 14.00 h and 15.00 h

| COMPOUND | DOSE (μmol/100 g) | DOSE (mg/kg) | FAT (min.) | ST (min.) | Sedation time (min.) |
| --- | --- | --- | --- | --- | --- |
| PLACEBO |   |   | NA–15 | 0–7 | 30–31 |
| DIAZEPAM | 1 | 2.85 | 4–5 | 50–117 | 0–18 |
| MELATONIN | 1 | 2.32 | 4–5 | 240–253 | 7–20 |
|   | 2 | 4.6 | 5–5 | 208–235 | 0–27 |
| Example 1 | 2 | 4.97 | 4–7 | 180–220 | 5–45 |

TABLE II

Tests under alternate lighting (light from 8.00 h to 20.00 h; darkness from 20.00 h to 8.00 h) with administration of the products between 14.00 h and 15.00 h

| COMPOUND | DOSE (μmol/100 g) | DOSE (mg/kg) | FAT (min.) | ST (min.) | Sedation time (min.) |
| --- | --- | --- | --- | --- | --- |
| PLACEBO |   |   | NA | 22 | 29 |
| DIAZEPAM | 1 | 2.48 | 13 | 36 | Not determined |
| MELATONIN | 1 | 2.32 | NA | 0 | 16–36 |
|   | 2 (3 batches) | 4.64 | NA | 0 | 54–77 |
| Example 1 | 2 | 4.97 | 10–15 | 40–77 | 15–32 |
| Example 2 | 2 | 5.24 | 10–15 | 50–80 | 10–25 |

Key:
NA: not applicable, the animals remain alert throughout the period of observation;
FAT: falling-asleep time equal to the time required to pass from the state of active wakefulness to a non-alert state;
ST: sleep time, equal to the duration of the period of sleep ranging from the point of having fallen asleep to the point of waking up;
Sedation time: following waking up, period of inactivity corresponding to stage 2 defined above.

Under the conditions in which the test is performed, in animals subjected to a program of alternate lighting, the hypnotic effect of melatonin is nil when it is administered between 14.00 h and 15.00 h (Table II).

By alternately subjecting chicks to programs of alternate and permanent lighting, we have demonstrated experimentally that melatonin has no direct hypnotic activity intrinsic to its structure. Its hypnotic activity depends on the activity of the enzyme N-acetyl transferase (NAT) in the pineal gland of the chick at the time of administration of the melatonin. The enzyme NAT is an acetylation enzyme. In the presence of the enzyme NAT in the pineal gland of the chick, during a program of permanent lighting, the IM administration of melatonin induces a hypnotic effect of strong intensity (sleep time of between 208 and 253 minutes for a dose of between 1 μmol and 2 μmol of melatonin/100 g of live weight). Melatonin is thus the precursor of acetylated metabolites having direct hypnotic activity, among which are featured the compounds of Examples 1 and 2.

The results obtained show, for the derivatives according to the invention, and in animals subjected to a program of alternate lighting, a hypnotic effect which is superior to that of the reference products (pentobarbital, melatonin) and equivalent to that of diazepam.

The compound of Example 1 (2-oxomelatonin) is the product of an oxidation of melatonin which might result from the reduction of free radicals. We have demonstrated its presence in the brain (pineal gland in particular) of sheep, sacrificed in the middle of the night, by gas chromatography/mass spectrometry coupling.

The derivatives according to the invention are thus particularly advantageous for the treatment of diseases associated with disorders of melatonin activity.

The present invention thus relates to the derivatives of general formula I, as defined above, for their use in therapy, in particular for the treatment of depression and psychiatric disorders, in particular stress, anxiety, depression, insomnia, schizophrenia, psychoses and epilepsy, and also for the treatment of sleeping disorders associated with travelling ("jet lag"), neurodegenerative diseases of the central nervous system such as Parkinson's disease or Alzheimer's disease, for the treatment of cancers, or alternatively as a contraceptive or as an analgesic.

The melatoninergic analogues according to the invention are also useful for the treatment of benign hyperplasia of the prostate, skin cancers, skin complaints such as psoriasis, acne, mycoses and glaucoma, as well as for increasing the immune resistance.

They are also useful for preventing the symptoms of menopause, pre-menstrual syndromes, the effects of aging and infant cot-death.

They are also useful in veterinary applications for controlling birth in ruminants.

The present invention thus relates also to the pharmaceutical compositions adapted for administration of the derivatives of general formula I, in particular via the oral, parenteral or rectal route, in the form of wafer capsules, tablets, gelatin capsules, drinkable solutions, injectable solutions, including delayed forms and sustained-release dressings for transdermal administration of the active principle, nasal sprays, or topical formulations (cream, emulsion, etc.), comprising a derivative of general formula I according to the invention and at least one pharmaceutically acceptable excipient.

The pharmaceutical compositions according to the invention are advantageously dosed to deliver the active principle in a single "delivery unit".

For oral administration, the effective unit doses are between 0.1 μg and 500 mg.

For intravenous administration, the effective unit doses are between 0.1 μg and 100 mg.

The melatoninergic analogues according to the invention are also useful in cosmetics, in particular for protecting the skin against aging, and also against hair loss.

The present invention thus relates also to a cosmetic composition comprising a derivative of general formula I according to the invention.

The cosmetic compositions according to the invention are formulated in an appropriate manner for their topical application, in particular in the form of ointments, creams, emulsions, salves, lotions, etc.

We claim:
1. A compound of general formula I

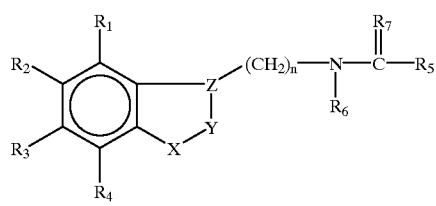

in which:

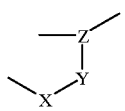

is selected from the group consisting of:

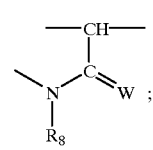

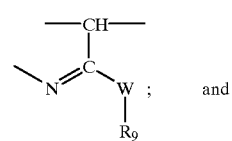

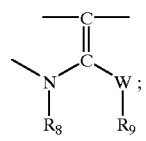

n is equal to 1, 2 or 3;

R1, R2, R3 and R4 represent, independently of each other, a hydrogen atom, a halogen atom, a hydroxyl group, a lower alkyl, cycloalkyl, lower alkoxy, aryloxy, lower aralkoxy, lower perhaloalkyl, lower perhaloalkoxy, or nitro group or an unsaturated aliphatic chain; or wherein R1 and R2, R2 and R3, and R3 and R4 form part of another aromatic or non-aromatic ring containing at least 5 atoms, wherein the ring optionally contains several hetero atoms and is optionally substituted with one or more groups that represent, independently of each other, a hydroxyl group, a lower alkyl, lower alkoxy, aryloxy, lower aralkoxy, or nitro group, a halogen atom, or an unsaturated aliphatic chain;

R5 represents a hydrogen atom, a lower alkyl, aryl or lower aralkyl group, each optionally substituted with one or more halogens, an amino, (lower) alkyl-amino or (lower) dialkyl-amino, arylalkylamino, aralkylamino, or diaralkylamino group, or a lower alkoxy, (lower) alkyloxycarbonyl, aryloxycarbonyl or aralkyloxycarbonyl group;

R6 and R8 represent, independently of each other, a hydrogen atom, a halogen atom, or a lower alkyl, aryl, lower aralkyl, lower alkoxy, aryloxy, lower aralkoxy, lower perhaloalkyl, (lower) perhaloalkyl-carbonyloxy, alkylsulphonyl, arylsulphonyl, aralkylsulphonyl, or (lower) perhaloalkylsulphonyl group;

W and R7 represent, independently of each other, an oxygen atom or a sulphur atom;

R9 represents a lower alkyl, aryl, or aralkyl group, optionally substituted with one or more halogens, an alkylcarbonyl, arylcarbonyl, aralkylcarbonyl, (lower) perhaloalkyl-carbonyl, or perhaloaralkylcarbonyl group, or a (lower) alkyl-sulphonyl, arylsulphonyl, aralkylsulphonyl, (lower) perhaloalkyl-sulphonyl or perhaloaralkylsulphonyl group; or wherein R5 and R6, R5 and R8, R6 and R8, and R8 and R9 are linked to form a saturated or unsaturated ring containing at least 5 atoms, wherein the ring optionally contains several hetero atoms and is optionally substituted with one or more groups, which represent, independently of each other, a hydroxyl group, a lower alkyl, lower alkoxy, aryloxy, lower aralkoxy, or nitro group, a halogen atom, or an unsaturated aliphatic chain;

their racemic mixtures, their pure enantiomers or their mixtures in all proportions, and their therapeutically acceptable salts.

2. The compound according to claim 1, wherein W and R7 each represent an oxygen atom and n is equal to 2.

3. The compound according to claim 1, wherein at least one of the substituents R2 or R3 is not a hydrogen atom.

4. The compound according to claim 1, wherein R1, R4, and R6 each represent a hydrogen atom.

5. The compound according to claim 1, wherein R8 or R9 represent, independently of each other, a hydrogen atom or a lower alkyl group.

6. A pharmaceutical composition, comprising a compound according to claim 1 and at least one pharmaceutically acceptable vehicle.

7. A cosmetic composition, comprising a compound according to claim 1 in combination with an ointment, a cream, an emulsion, a salve, or a lotion.

8. The compound according to claim 1, wherein n is 2.

9. The compound according to claim 3, wherein at least one of the substituents R2 or R3 represents a hydroxyl or lower alkoxy group.

10. The compound according to claim 3, wherein at least one of the substituents R2 or R3 is a methoxy group.

11. A compound according to claim 2, wherein at least one of the substituents R2 or R3 is a methoxy group.

12. The compound according to claim 3, wherein R1, R4, and R6 represents a hydrogen atom.

13. The compound according to claim 4, wherein R8 or R9 represents a hydrogen atom or a lower alkyl group.

14. The compound according to claim 1, wherein R5 and R6, R5 and R8, R6 and R8, or R8 and R9 are linked to form a saturated or unsaturated ring containing 6 atoms.

15. The compound according to claim 1, wherein R1 and R2, R2 and R3, or R3 and R4 form part of an aromatic or non-aromatic ring with or without a hetero atom containing 6 atoms.

16. The compound according to claim 1, wherein said compound is selected from the group consisting of: N-(2-(5-methoxy-2-oxo-2,3-dihydroindol-3-yl)ethyl)acetamide, and N-(2(5-methoxy-1-methyl-2-oxo-2,3-dihydroindol-3-yl)ethyl)acetamide.

17. A method for treating a disease associated with disorders of melatonin activity, said method comprising administering a therapeutically effective dose of the pharmaceutical composition of claim 6 to a patient.

18. The method of claim 17, wherein said pharmaceutical composition is administered orally and the therapeutically effective dose is between 0.1 μg and 500 mg.

19. The method of claim 17, wherein said pharmaceutical composition is administered intravenously and the therapeutically effective dose is between 0.1 μg and 100 mg.

* * * * *